(12) United States Patent
David

(10) Patent No.: US 7,696,889 B2
(45) Date of Patent: Apr. 13, 2010

(54) FLUID LEAK DETECTION SYSTEM AND ASSOCIATED METHOD

(76) Inventor: Woodrow J. David, 11345 Skimmer Ct., Jacksonville, FL (US) 32225

( * ) Notice: Subject to any disclaimer, the term of this patent is extended or adjusted under 35 U.S.C. 154(b) by 357 days.

(21) Appl. No.: 11/973,665

(22) Filed: Oct. 9, 2007

(65) Prior Publication Data
US 2009/0091460 A1    Apr. 9, 2009

(51) Int. Cl.
| G08B 21/00 | (2006.01) |
| B67D 5/60 | (2006.01) |
| B67B 7/00 | (2006.01) |
| A47L 15/46 | (2006.01) |
| H01H 29/00 | (2006.01) |
| C02F 5/02 | (2006.01) |
| G01M 3/04 | (2006.01) |
| A47K 13/00 | (2006.01) |

(52) U.S. Cl. ............ 340/605; 340/612; 340/618; 222/145.1; 222/1; 222/651; 200/61.04; 252/176; 73/40; 4/233

(58) Field of Classification Search .......... 340/605, 340/612, 618; 222/145.1, 1, 651; 200/61.04; 252/176; 73/40; 4/233
See application file for complete search history.

(56) References Cited

U.S. PATENT DOCUMENTS

| 4,378,014 A | * | 3/1983 | Elkow | 604/48 |
| 4,841,282 A | * | 6/1989 | Reis | 340/521 |
| 4,888,455 A | | 12/1989 | Hanson | |
| 6,349,440 B1 | * | 2/2002 | Amberg et al. | 8/158 |
| 6,874,697 B2 | * | 4/2005 | Callueng | 239/1 |
| 6,950,032 B1 | | 9/2005 | Hewitt et al. | |
| 7,114,514 B2 | | 10/2006 | Houle | |
| 7,320,418 B2 | * | 1/2008 | Sassoon | 222/649 |
| 2003/0011482 A1 | * | 1/2003 | Harms et al. | 340/605 |

* cited by examiner

*Primary Examiner*—George A Bugg
*Assistant Examiner*—Jack Wang
(74) *Attorney, Agent, or Firm*—Arthur G. Yeager

(57) ABSTRACT

A fluid leak detection system includes a reservoir, a predetermined quantity of a disinfecting liquid contained within such a reservoir, and at least a pair of elongated conduits. A mechanism for automatically opening the distal end of the at least one conduit includes a leaking fluid absorbent member disposed along the distal end of each of the conduits. The fluid-dissolvable member is dissolved by the leaking fluid and absorbed by the member to permit the conduit to be unfolded and allow the disinfecting liquid to flow outwardly from the distal end of the at least one conduit. The system further includes a support frame attached to a support surface, an interface, a communications device electrically coupled to a switch, a monitoring station, and a communications link connecting the communications device to the monitoring station.

20 Claims, 5 Drawing Sheets

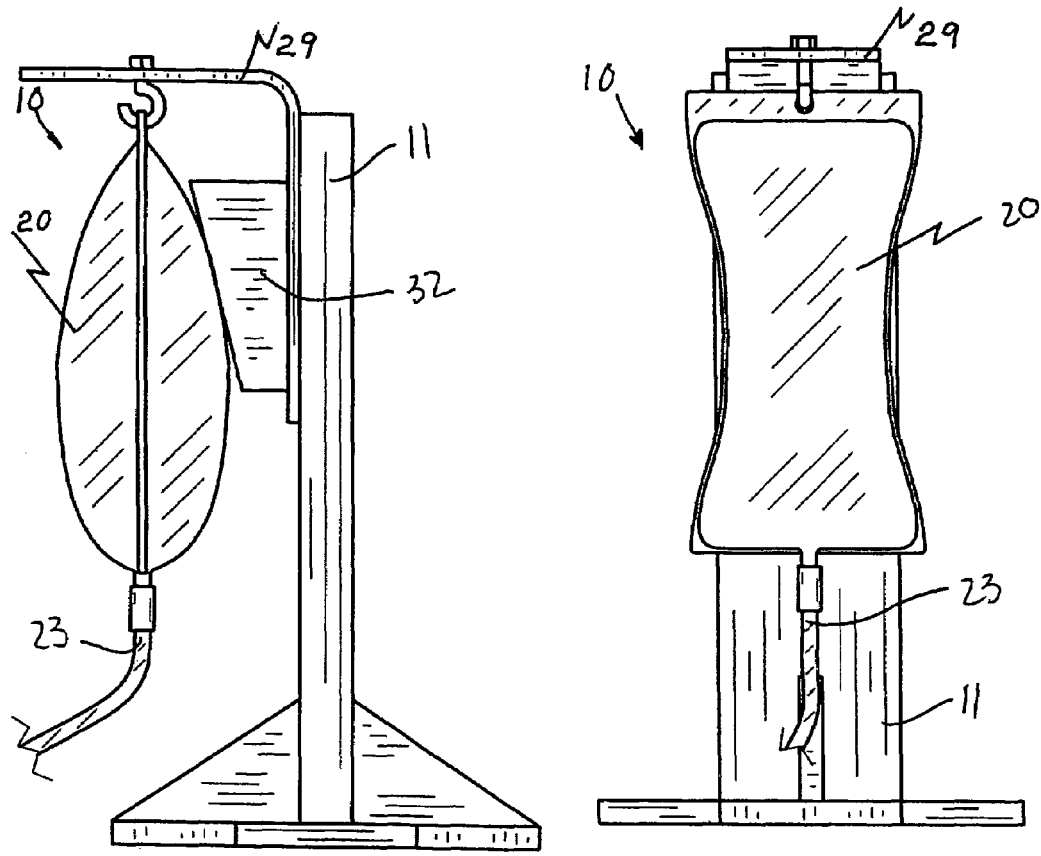
FIG. 2                    FIG. 3
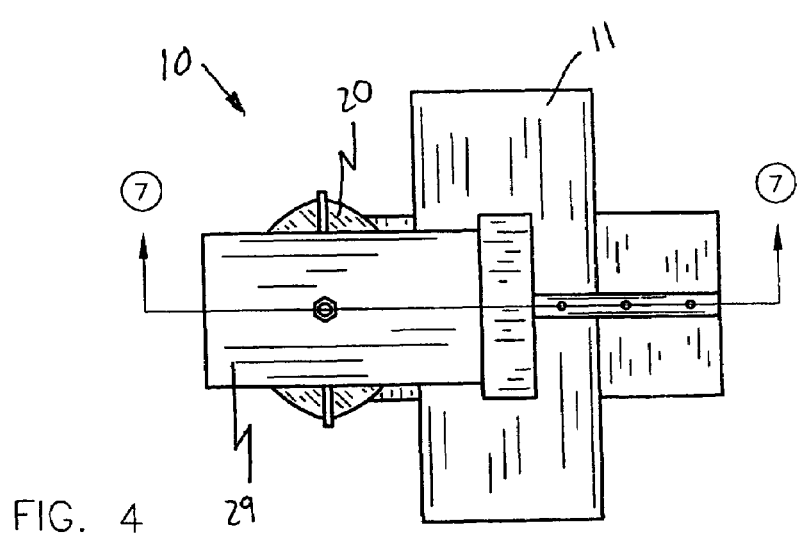
FIG. 4

FLUID LEAK DETECTION SYSTEM AND ASSOCIATED METHOD

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to leak detecting systems and, more particularly, to a fluid leak detection system for substantially preventing mold and mildew growth and associated methods. The fluid leaking is commonly water in a water supply and return system.

2. Prior Art

As most people are probably aware, every year homeowners, businesses and insurance companies spend hundreds of millions of dollars repairing mold and mildew damage caused by leaking fluids, primarily water. The effects of such damages on health related issues are uncounted and unimaginable suffering. A problem that began as just a few drips per minute damages property and more significantly the health and well being of entire populaces of homes and buildings.

At just ten drips per minute, a puddle forms, expands and begins to travel due to construction imperfections and an effect known as capillary attraction. As the puddle of leakage or condensation travels, it begins to be absorbed into the surrounding building materials where it incubates mold and mildew. The mold and mildew consume the building as food as it begins to deteriorate the property. It then matures, branches out, and releases countless numbers of spores. Mold and mildew simply requires a temperature above 60° F., 20% humidity and the nutrients found in all natural materials to flourish.

Even when the conditions that initiated the mold and mildew are repaired, the residual moisture and the moisture in the air permits mold and mildew to thrive and therefore remain a health risk. Once the spores are exposed to open areas, the air conditioning and heating system spread the spores to further enhance the spread of mold and mildew in its quest for domination of the building.

The two major elements in preventing mold and mildew growth are timely discovery and immediate treatment of the affected area. Timely discovery requires discovery of the problem within 24 to 48 hours, and adequate treatment requires that a chemical agent is supplied to the leak from the onset of the problem. The primary areas of water leaks and condensation problems include: wall cavities that contain plumbing; cabinets with sinks; basements; dishwashers; water heaters; icemakers; washing machines; and attics. Due to the variations in construction methods, some leaks may never be detected unless a professional or a detection device discovers it. The size of an average leak before it is detected is approximately 38 square feet and contains 9 to 14 gallons of water, and which has been producing spores for several days. Obviously, it would be advantageous for a user to have a detection device and system that would alert them of a leak while simultaneously preventing the spread of bacteria in a user building.

U.S. Pat. No. 4,888,455 to Hanson discloses, in the absence of moisture, a separation between a pair of electrical contacts maintained by a material that becomes frangible when moistened. When the material becomes moist, it breaks and the contacts close. Unfortunately, this prior art example does not provide a user with an audible alarm or a way to counteract mold and mildew growth when a leak occurs.

U.S. Pat. No. 6,950,032 to Hewitt discloses a water protection system apparatus for detecting and stopping a flow of water which includes a power supply, a water ionization switch, and a controlled valve assembly. The water ionization switch selectively conducts electricity when exposed to water and includes an initially dry non-conductive crystallized compound. The compound ionizes when exposed to water to form an electrolyte which conducts electricity. This switch is connected to a controlled valve assembly to stop the flow of water in response to the detection of water by the switch. Other refinements include modifications to the switch housing and condition indicators for monitoring the system and signaling water detection and shutdown operations. Unfortunately, this prior art example does not automatically and substantially kill all bacteria or spores that may spread from leaked water.

U.S. Pat. No. 7,114,514 to Houle discloses a water management and leak detection with a containment system to contain hot water tank leaks and electrical circuits that manage water flow and electricity to the hot water tank. Unfortunately, this prior art example does not provide a user with an audible alarm when a leak occurs, for example, nor the other benefits of the disclosed invention.

Accordingly, the present invention overcomes the above noted shortcomings. The present invention satisfies such a need by providing a system and method that is convenient, easy to use, and designed for substantially preventing mold and mildew growth caused by a leaking fluid.

BRIEF SUMMARY OF THE INVENTION

In view of the foregoing background, it is therefore an object of the present invention to provide an apparatus and method for substantially preventing mold and mildew growth. These and other objects, features, and advantages of the invention are provided by a fluid leak detection system.

A fluid leak detection system includes a reservoir, a predetermined quantity of a disinfecting liquid contained within such a reservoir, and at least one elongated conduit having one end in fluid communication with the reservoir and with a distal end in an initial closed position. Such distal end is effectively located downstream of the reservoir and is spacedly disposed in a remote location likely within an area of a leaking fluid. Preferably, there are at least two conduits that are respectively located in spaced areas where the leaking fluid is likely to travel, so that the leaking fluid does not escape detection, etc.

The system further includes a mechanism for automatically opening the distal end of the at least one conduit to an open position upon detecting a leaking fluid disposed on a surface external of the at least one conduit such that the disinfecting liquid automatically discharges from the distal end of at least one conduit and conveniently encounters the detected fluid to substantially prevent mold and mildew growth. The distal end of the at least one conduit remains statically engaged with the reservoir when the distal end of the at least one conduit is opened.

The mechanism includes a leaking fluid absorbent member disposed along the distal end of each of the conduits. Such a fluid absorbent member advantageously extends along a partial longitudinal length of the at least one conduit and spans outwardly therefrom. Each distal end is folded onto an adjacent portion of the conduit, and a leaking fluid-dissolvable member is wrapped about the distal end and the adjacent portion of the conduits such that the disinfecting liquid is prohibited from egression outwardly of the distal ends. The fluid-dissolvable member effectively becomes saturated with the leaking fluid after the fluid absorbent member becomes saturated by the leaking fluid. The fluid-dissolvable member is dissolved by the leaking fluid and absorbed by the member to permit the conduit to be unfolded and allow the disinfecting liquid to flow outwardly from the distal end of at least one conduit.

The system further includes a support frame attached to a support surface. The reservoir is conveniently anchored to the support frame and maintained at an elevated position above the distal ends of the conduits so that the disinfecting liquid is allowed to freely flow downstream along at least one conduit after the distal end is in the open position. The disinfecting liquid is an antimicrobial liquid to prevent mold and mildew growth. The system further includes an electrical switch located between the reservoir and the support surface, and a low voltage electrical source and an alarm. Such a switch advantageously becomes open upon general depletion of the disinfecting liquid in the reservoir and activates the alarm.

The fluid leak detection system further includes an interface electrically coupled to an existing fluid source control valve of the leaking fluid. The switch, when open, effectively activates the interface upon detecting the leaking fluid, and the interface turns the control valve of the leaking fluid to a closed position for eliminating continuance of the leaking fluid.

The system further includes a communications device electrically coupled to the switch, a monitoring station, and a communications link connecting the communications device to the monitoring station. Such a communications device automatically notifies the monitoring station of the leaking fluid when the switch activates the communication device.

A method for substantially preventing mold and mildew growth includes the steps of: providing the reservoir; depositing a predetermined quantity of a disinfecting liquid into the reservoir; connecting one end of at least one conduit to the reservoir; closing a distal end of the at least one conduit to an initial closed position by folding the distal end onto an adjacent portion of the at least one conduit; and automatically opening the distal end of the at least one conduit to an open position upon detecting a leaking fluid disposed on a surface external of the at least one conduit such that the disinfecting liquid automatically discharges from the distal end and encounters the detected fluid to substantially prevent mold and mildew growth.

The method further includes the steps of: wrapping a leaking fluid-dissolvable member about the distal end and the adjacent portion of the at least one conduit such that the disinfecting liquid is prohibited from egress outwardly of the distal end; disposing a leaking fluid absorbent member along the distal end of the at least one conduit by extending outwardly the leaking fluid absorbent member along a partial longitudinal length of the at least one conduit; dissolving the fluid-dissolvable member when the fluid-dissolvable member becomes saturated and thereby permitting the at least one conduit to be unfolded; and allowing the disinfecting liquid to flow outwardly from the distal end of the at least one conduit.

The method further includes the steps of: disposing a support frame on a support surface that is adjacent an area likely to have a leaking fluid; anchoring the reservoir to the support frame; and maintaining the reservoir at an elevated position above the distal end of the conduit so that the disinfecting liquid is allowed to freely flow downstream along the at least one conduit after the distal end is in the open position. The steps further include: locating an electrical switch between the reservoir and the support surface; connecting a low voltage electrical source to an alarm; and opening the switch upon general depletion of the disinfecting liquid in the reservoir and activating the alarm.

The method further includes the steps of: electrically coupling an interface to an existing fluid source control valve of the leaking fluid; when the switch is open, activating the interface upon detecting the leaking fluid; and the interface turning the control valve of the leaking fluid to a closed position for eliminating continuance of the leaking fluid. The steps further include the steps of: electrically connecting a communications device to the switch; establishing a communications link between a monitoring station and the communications link; and the communications device automatically notifying the monitoring station of the leaking fluid when the switch activates the communication device.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

FIG. 2 is a partial side elevational view of a fluid leak detection system;

FIG. 3 is a partial front elevational view of a fluid leak detection system;

FIG. 4 is a partial top planar view of a fluid leak detection system;

DETAILED DESCRIPTION OF THE INVENTION

Figure 1:
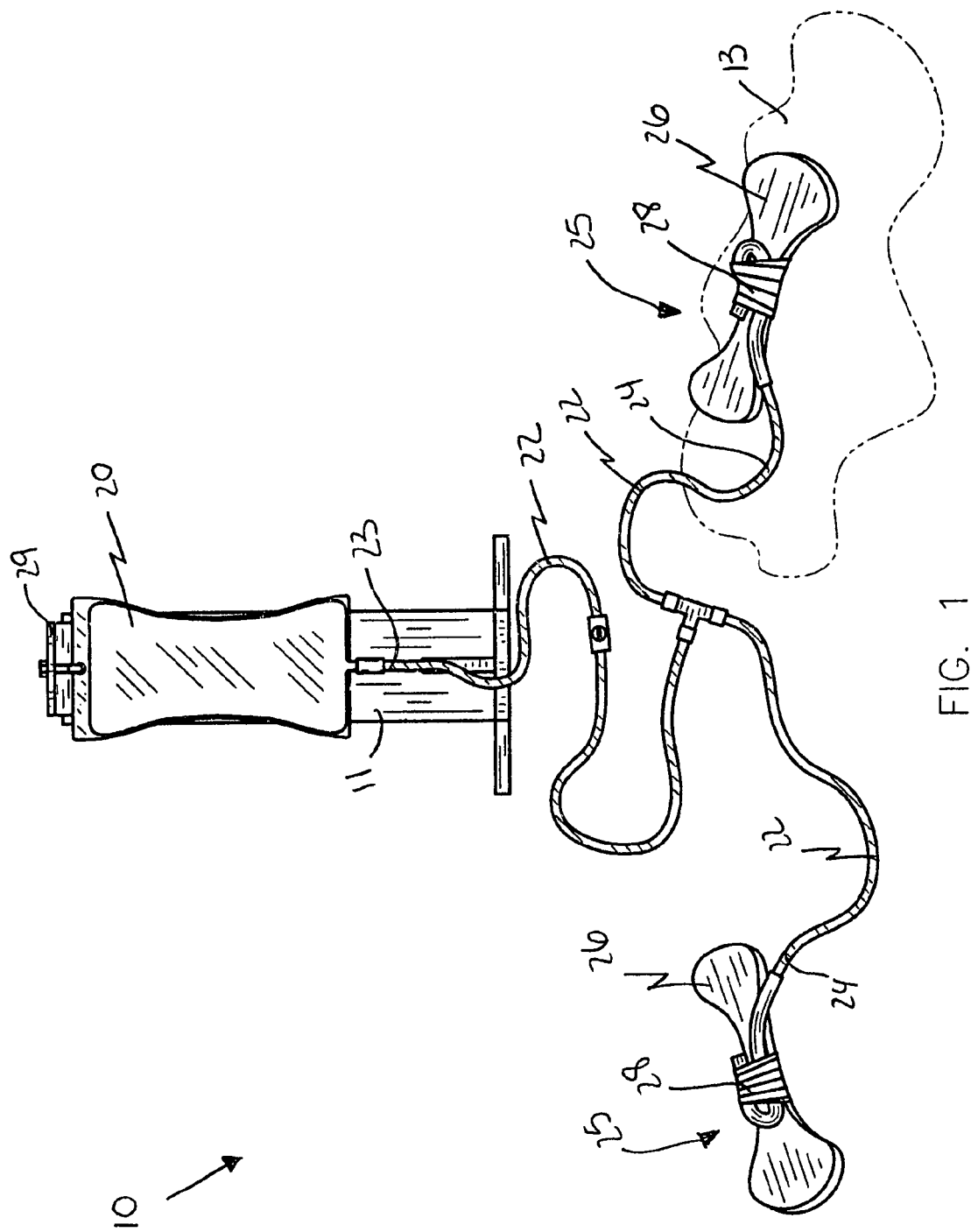
FIG. 1 is a perspective view showing a fluid leak detection system, in accordance with the present invention.

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The system of this invention is referred to generally in FIGS. 1-8 by the reference numeral 10 and is intended to protect a fluid leak detection system. It should be understood that the system 10 may be used to protect many different types of fluid containing reservoirs and should not be limited in use with only those reservoirs mentioned herein.

Referring initially to FIGS. 1, 2, 3 and 7, a fluid leak detection system 10 includes a reservoir 20, a predetermined quantity of a disinfecting liquid 21 contained within such a reservoir 20, and at least a pair of elongated conduits 22 each having one end 23 in fluid communication with the reservoir and with a distal end 24 in an initial closed position. Each of such distal ends 24 is effectively located downstream of the reservoir 20 and is disposed spacedly in respective remote locations. The disinfecting liquid 21 is for killing bacteria in the leaking fluid, thereby reducing the potential spread of the bacteria and microorganisms to other areas of the house.

Figure 5:
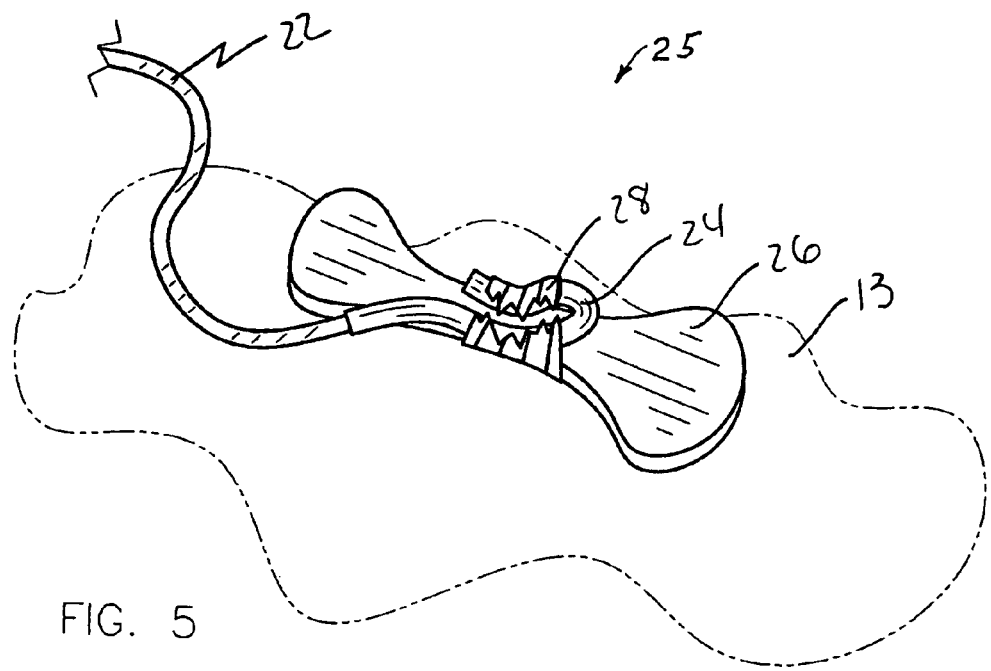
FIG. 5 is a perspective view of the automatically opening mechanism beginning to dissolve in a leaking fluid, in accordance with the present invention.
Figure 6:
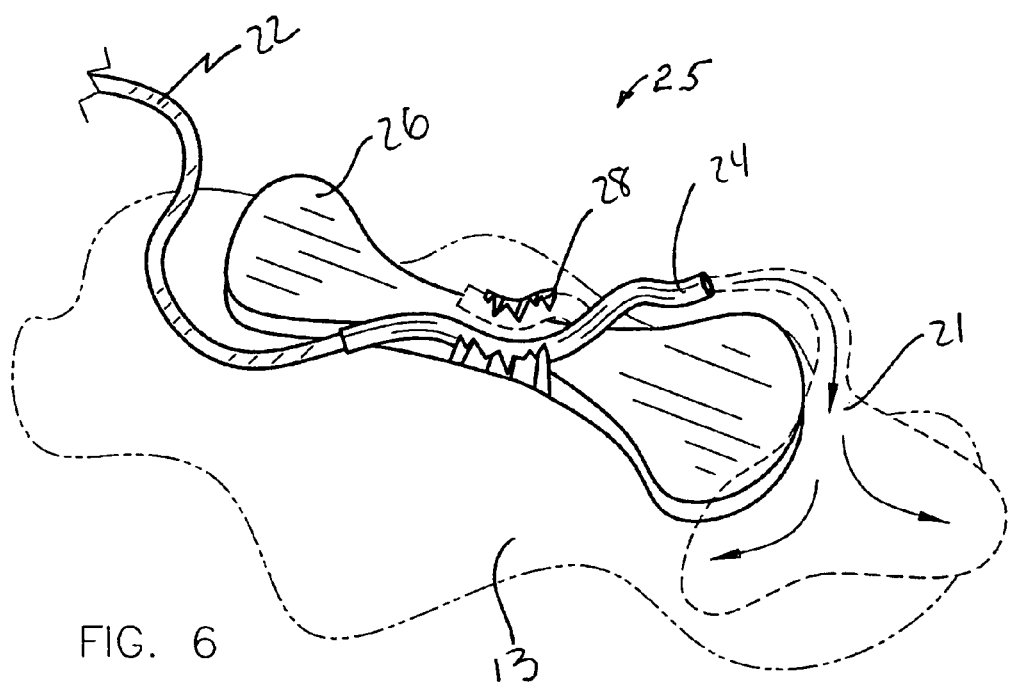
FIG. 6 is a perspective view of the automatically opening mechanism dispensing a disinfecting liquid.
Figure 7:
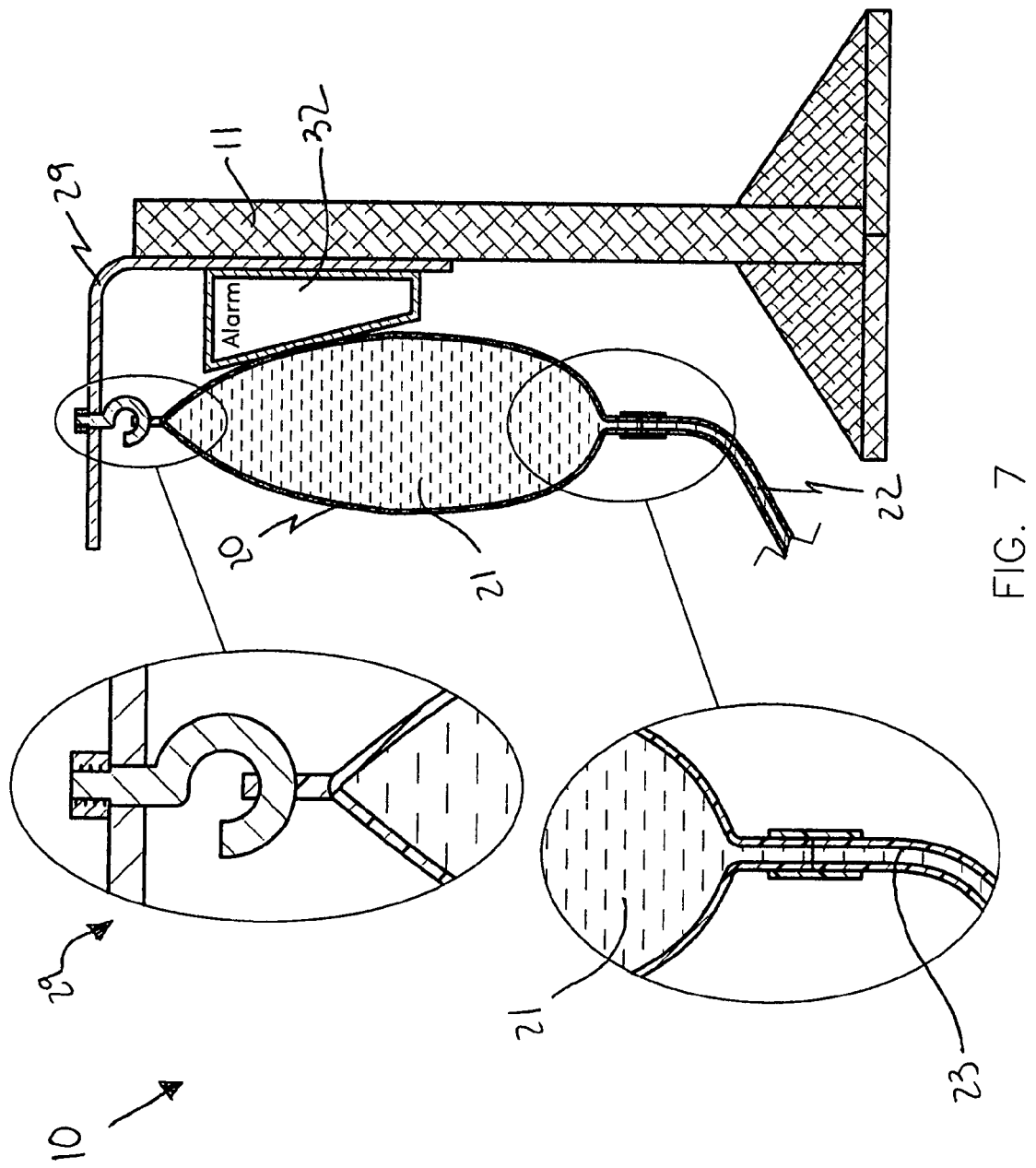
FIG. 7 is a cross sectional view, taken along line 7-7, as seen in FIG. 4.

Referring to FIGS. 1, 5 and 6, the system 10 further includes a mechanism 25 for automatically opening the distal end 24 of the at least one conduit 22 to an open position upon detecting a leaking fluid disposed on a surface external of the at least one conduit 22 which is crucial such that the disinfecting liquid 21 automatically discharges from the distal end 24 of the at least one conduit 22 and conveniently encounters the detected fluid to substantially prevent mold and mildew growth. The distal end 24 of the at least one 22 conduit remains statically engaged with the reservoir 20 when the distal end 24 of the at least one conduit 22 is opened. The mechanism 25 ensures that the disinfecting liquid 21 is not discharged from the reservoir 20 until a leak occurs.

Referring again to FIGS. 1, 5 and 6, the mechanism includes a leaking fluid absorbent member 26 disposed along the distal end 24 of each of the conduits 22. Such a fluid absorbent member 26 advantageously extends along a partial longitudinal length of the at least one conduit 22 and spans outwardly therefrom. Each distal end 24 is folded onto an adjacent portion of the conduit 22, and a leaking fluid-dissolvable member 28 is wrapped about the distal end 24 and the adjacent portion of the conduits 22 which is important such that the disinfecting liquid 21 is prohibited from egressing outwardly of the distal ends 24. The fluid-dissolvable member 28 effectively becomes saturated with the leaking fluid 13 after the fluid absorbent member 28 becomes saturated by the leaking fluid. The fluid-dissolvable member 28 is dissolved by the leaking fluid and absorbed by the member 28 to permit the one conduit 22 to be unfolded and allow the disinfecting liquid 21 to flow outwardly from the distal end 24 of the at least one conduit 22. When a leak occurs, the fluid-dissolvable member 28 disintegrates and releases the distal end 24 of the conduit 22, thereby allowing the disinfecting liquid 21 to spread throughout the leaking fluid 13.

Referring to FIGS. 1, 2, 3, 4, 7 and 8, the system 10 further includes a support frame 29 attached to a support surface 11. The reservoir 20 is anchored to the support frame 29 and maintained at an elevated position above the distal ends 24 of the conduits 22 so that the disinfecting liquid 21 is allowed to freely flow downstream along the at least one conduit 22 after the distal end 24 is in the open position. The disinfecting liquid 21 is an antimicrobial liquid to prevent mold and mildew growth. The system 10 further includes an electrical switch 30 located between the reservoir 20 and the support surface 11, and a low voltage electrical source 31 and an alarm 32. Such a switch 30 becomes open upon general depletion of the disinfecting liquid 21 in the reservoir 20 and activates the alarm 32. The support frame 29 suspends the reservoir 20 above a ground surface to ensure that when a conduit 22 is opened, the disinfecting agent 21 can flow freely from the reservoir 20.

Figure 8:
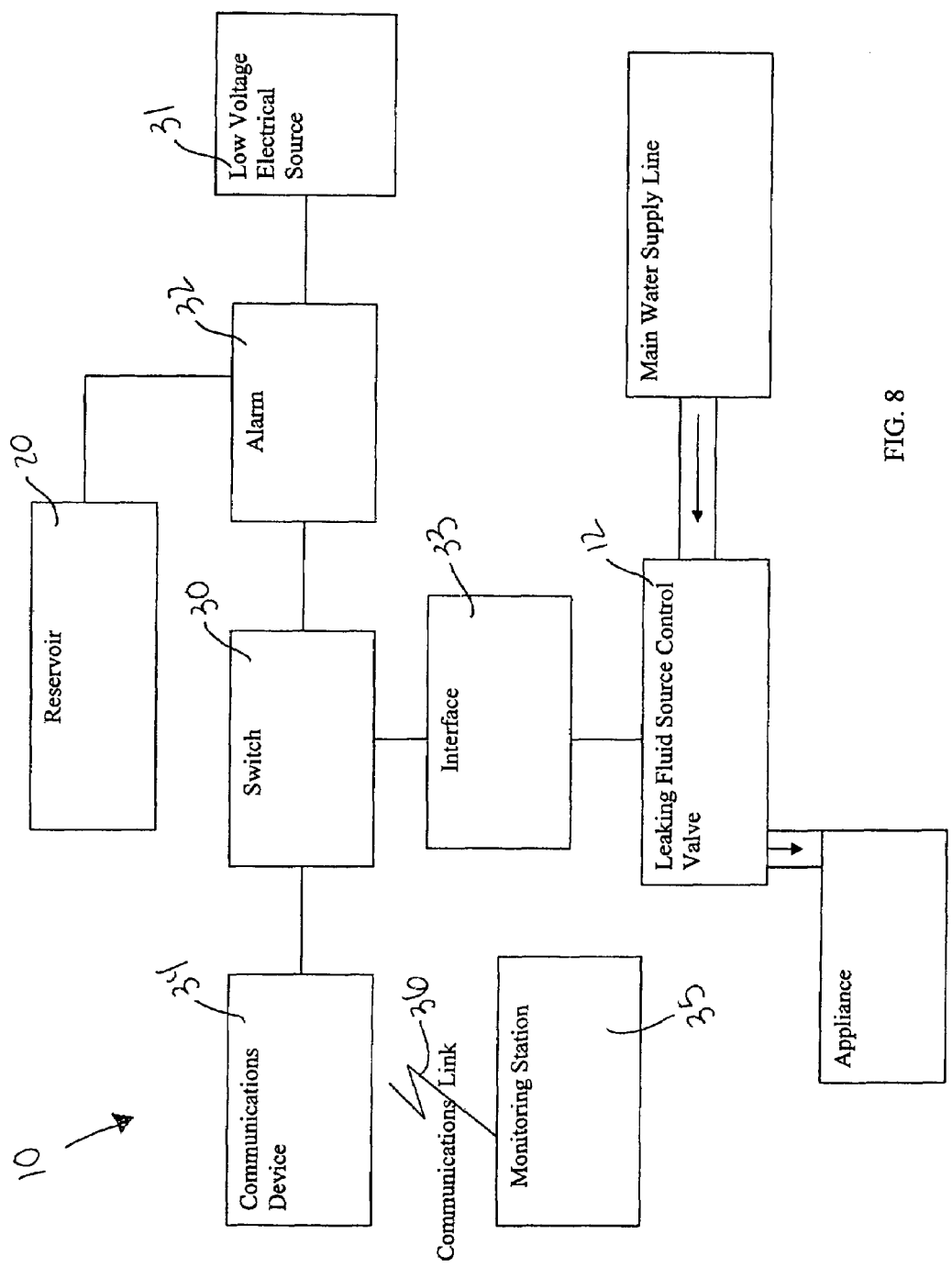
FIG. 8 is a schematic block diagram of a fluid leak detection system, in accordance with the present invention.

Referring to FIG. 8, the fluid leak detection system 10 further includes an interface 33 electrically coupled to an existing fluid source control valve 12 of the leaking fluid. The switch 30, when open, activates the interface 33 upon detecting the leaking fluid, and the interface 33 turns the control valve 12 of the leaking fluid 13 to a closed position for eliminating continuance of the leaking fluid 13.

Referring again to FIG. 8, the system 10 further includes a communications device 34 electrically coupled to the switch 30, a monitoring station 35, and a communications link 36 connecting the communications device 34 to the monitoring station 35. Such a communications device 34 automatically notifies the monitoring station 35 of the leaking fluid when the switch 30 activates the communication device 34.

The sooner a leak is detected the more effective a remedy will be once a leak has begun. The water under a cabinet, for instance, puddles or spatters into an ever growing and undetected area. As the wetness spreads, absorbers direct the moisture to open which then floods the area with a non-toxic child and pet friendly chemical agent that spreads through the water to eliminate and kill molds, mildews, and bacteria. As the reservoir level drops, an audible alarm sounds to inform a user to turn off the water supply and call the plumber.

The most destructive type of leak is the slow drip leak whose water buildup is solely contained under walls, carpet padding, cabinets, crawl spaces or ceiling and floor structures and grows mold undisturbed. The present invention is easy to install with only periodic battery replacement and the addition of water for evaporation concerns.

The present invention, as claimed, provides the unexpected and unpredictable benefit of a system that distributes an antimicrobial when a leak occurs and at the most strategic leak areas. In addition, the system is non-toxic and is therefore child and pet friendly. The automatic sensor and dispenser will have prolonged alarm capabilities. Such benefits overcome the prior art shortcomings.

The system will protect both a user's health and home from mold and mildew growth. The system is compact and hidden, therefore detracting nothing from the décor. The system is easy to install, safe, and will prevent health and home damage. In addition, the system is affordable, and the anti-microbial is designed to last for 2 years. The alarm can be used multiple times without needing battery replacement. The reservoir, conduits and valve may be disposable or refillable.

The valve head should be placed within 3 feet of a leak. When the valve opens, the anti-microbial agent floods the area of the leak. The chosen agent is effective at 3000 ppm. The Brownian motion, a vibration found in liquids; is caused by liquid molecules bouncing off one another, which distributes the agent throughout the leak puddle, and as the leak water grows and travels, so does the agent.

The system may be used with various water systems that may sprout a leak, including but not limited to: adjacent hot water heaters; cooling towers; kitchen sink cabinets; bath sink cabinets; dishwasher; ice maker; and washing machines. The system may also be used anywhere that may present a water leak in homes, apartments, condos or businesses.

In use, a method for substantially preventing mold and mildew growth includes the steps of: providing the reservoir 20; depositing a predetermined quantity of a disinfecting liquid 21 into the reservoir 20; connecting one end 23 of at least one conduit 22 to the reservoir 20; closing a distal end 24 of the at least one conduit 22 to an initial closed position by folding the distal end 24 onto an adjacent portion of the at least one conduit 22; and automatically opening the distal end 24 of the at least one conduit 22 to an open position upon detecting a leaking fluid disposed on a surface external of the at least one conduit 22 such that the disinfecting liquid 21 automatically discharges from the distal end 24 and encounters the detected fluid 13 to substantially prevent mold and mildew growth.

In use, the method further includes the steps of: wrapping a leaking fluid-dissolvable member 28 about the distal end 24 and the adjacent portion of the at least one conduit 22 such that the disinfecting liquid 21 is prohibited from egress outwardly of the distal end 24; disposing a leaking fluid absorbent member 26 along the distal end 24 of the at least one conduit 22 by extending outwardly the leaking fluid absorbent member 26 along a partial longitudinal length of the at least one conduit 22; dissolving the fluid-dissolvable member 26 when the fluid-dissolvable member 26 becomes saturated and thereby permitting the at least one conduit 22 to be unfolded; and allowing the disinfecting liquid 21 to flow outwardly from the distal end 24 of the at least one conduit 22.

In use, the method further includes the steps of: disposing a support frame 29 on a support surface 11 adjacent an area likely to have a leaking fluid anchoring the reservoir 20 to the support frame 29; and maintaining the reservoir 20 at an elevated position above the distal end 24 of the conduit 22 so that the disinfecting liquid 21 is allowed to freely flow downstream along the at least one conduit 22 after the distal end 24 is in the open position. The steps further include: locating an electrical switch 30 between the reservoir 20 and the support surface 11; connecting a low voltage electrical source 31 to an alarm 32; and opening the switch 30 upon general depletion of the disinfecting liquid 21 in the reservoir 20 and activating the alarm 32.

In use, the method further includes the steps of: electrically coupling an interface 33 to an existing fluid source control valve 12 of the leaking fluid 13; when the switch 30 is open, activating the interface 33 upon detecting the leaking fluid 13; and the interface 33 turning the control valve 12 of the leaking fluid to a closed position for eliminating continuance of the leaking fluid 13. The steps further include the steps of: electrically connecting a communications device 34 to the switch 30; establishing a communications link 36 between a monitoring station 35 and the communications link 36; and the communications device 34 automatically notifying the monitoring station 35 of the leaking fluid when the switch 30 activates the communication device 34.

The sooner a leak is detected the more effective a remedy will be once a leak has begun. The water under a cabinet, for instance, puddles or spatters into an ever growing and undetected area. As the wetness spreads, absorbers direct the moisture to open the valve which then floods the area with a non-toxic child and pet friendly chemical agent that spreads through the water to eliminate and kill molds, mildews, and bacteria. As the reservoir level drops, an audible alarm sounds to inform a user to turn off the water supply and call the plumber.

The most destructive type of leak is the slow drip leak whose water buildup is solely contained under walls, carpet padding, cabinets, crawl spaces or ceiling and floor structures and grows mold undisturbed. The present invention is easy to install with only periodic battery replacement and the addition of water for evaporation concerns.

The present invention, as claimed, provides the unexpected and unpredictable benefit of a system that distributes an antimicrobial when a leak occurs and at the most strategic leak areas. In addition, the system is non-toxic and is therefore child and pet friendly. The automatic sensor and dispenser will have prolonged alarm capabilities. Such benefits overcome the prior art shortcomings.

The system will protect both a user's health and home from mold and mildew growth. The system is compact and hidden, therefore detracting nothing from the décor. The system is easy to install, safe, and will prevent health and home damage. In addition, the system is affordable, and the anti-microbial is designed to last for 2 years. The alarm can be used multiple times without needing battery replacement.

The valve head should be placed within 3 feet of a leak-prone area as described. When the valve opens, the anti-microbial agent floods the area of the leak. The chosen agent is effective at 3000 ppm. The Brownian motion, a vibration found in liquids including water, distributes the agent throughout the leak puddle, and as the leak water grows and travels, so does the agent.

The system may be used with various water systems that may sprout a leak, including but not limited to: adjacent hot water heaters; cooling towers; ductwork, kitchen sink cabinets; bath sink cabinets; dishwasher; ice maker; and washing machines. The system may also be used anywhere that may present a water leak in homes, apartments, condos or businesses.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A fluid leak detection system for substantially preventing mold and mildew growth, said fluid leak detection system comprising: a reservoir; a predetermined quantity of a disinfecting liquid contained within said reservoir; at least one conduit having one end in fluid communication with said reservoir and having a distal end in an initial closed position; means for automatically opening said distal end of said at least one conduit to an open position upon detecting a leaking fluid disposed on a surface external of said at least one conduit such that said disinfecting liquid automatically discharges from said distal end and encounters the detected fluid to substantially prevent mold and mildew growth; and an alarm being activated upon detection of general depletion of said disinfecting liquid in said reservoir.

2. The fluid leak detection system of claim 1, wherein said system further includes:
- a leaking fluid absorbent member disposed along said distal end of said at least one conduit, said fluid absorbent member extending along a partial longitudinal length of said at least one conduit and spanning outwardly therefrom;
- said distal end being folded onto an adjacent portion of said at least one conduit;
- a leaking fluid-dissolvable member wrapped about said distal end and said adjacent portion of said at least one conduit such that said disinfecting liquid is prohibited from egress outwardly of said distal end;
- said fluid-dissolvable member becoming saturated with the leaking fluid after said fluid absorbent member becomes saturated by the leaking fluid, said fluid-dissolvable member being dissolved by the leaking fluid and absorbed by said member to permit said at least one conduit to be unfolded and allowing said disinfecting liquid to flow outwardly from said distal end of said at least one conduit.

3. The fluid leak detection system of claim 2, further including:
- a support frame attached to a support surface, said reservoir being anchored to said support frame and maintained at an elevated position above said distal end of said conduit so that said disinfecting liquid is allowed to freely flow downstream along said at least one conduit after said distal end is in said open position.

4. The fluid leak detection system of claim 3, further including an electrical switch located between said reservoir and said support surface, a low voltage electrical source, said switch becoming open upon general depletion of said disinfecting liquid in said reservoir and activating said alarm.

5. The fluid leak detection system of claim 4, further including:
- an interface electrically coupled to an existing fluid source control valve of the leaking fluid;
- said switch when open activates said interface upon detecting the leaking fluid, said interface turning said control valve of the leaking fluid to a closed position for eliminating continuance of the leaking fluid.

6. The fluid leak detection system of claim 4, further including:
- a communications device electrically coupled to said switch;
- a monitoring station; and
- a communications link connecting said communications device to said monitoring station;
- said communications device automatically notifying said monitoring station of the leaking fluid when said switch activates said communication device.

7. The fluid leak detection system of claim 1, wherein said disinfecting liquid is an antimicrobial liquid to prevent mold and mildew growth.

8. A fluid leak detection system for substantially preventing mold and mildew growth, said fluid leak detection system comprising: a reservoir; a predetermined quantity of a disinfecting liquid contained within said reservoir; at least a pair of elongated conduits each having one end in fluid communication with said reservoir and having a distal end in an initial closed position, each of said distal ends being located downstream of said reservoir and being spacedly disposed in remote locations; means for automatically opening said distal end of said at least one conduit to an open position upon detecting a leaking fluid disposed on a surface external of said at least one conduit such that said disinfecting liquid automatically discharges from said distal end of said at least one conduit and encounters the detected fluid to substantially prevent mold and mildew growth, said distal end of said at least one conduit remaining statically engaged with said reservoir when said distal end of said at least one conduit is opened; and an alarm being activated upon detection of general depletion of said disinfecting liquid in said reservoir.

9. The fluid leak detection system of claim 8, wherein said system further includes:
- a leaking fluid absorbent member disposed along said distal end of each of the conduits, said fluid absorbent member extending along a partial longitudinal length of said at least one conduit and spanning outwardly therefrom;
- each said distal end being folded onto an adjacent portion of said conduit;
- a leaking fluid-dissolvable member wrapped about said distal end and said adjacent portion of said conduits such that said disinfecting liquid is prohibited from egress outwardly of said distal ends;
- said fluid-dissolvable member becoming saturated with the leaking fluid after said fluid absorbent member becomes saturated by the leaking fluid, said fluid-dissolvable member being dissolved by the leaking fluid and absorbed by said member to permit said one conduit to be unfolded and allowing said disinfecting liquid to flow outwardly from said distal end of said at least one conduit.

10. The fluid leak detection system of claim 7, further including:
- a support frame attached to a support surface, said reservoir being anchored to said support frame and maintained at an elevated position above said distal ends of said conduits so that said disinfecting liquid is allowed to freely flow downstream along said at least one conduit after said distal end is in said open position.

11. The fluid leak detection system of claim 10, further including an electrical switch located between said reservoir and said support surface, a low voltage electrical source and an alarm, said switch becoming open upon general depletion of said disinfecting liquid in said reservoir and activating said alarm.

12. The fluid leak detection system of claim 11, further including:
- an interface electrically coupled to an existing fluid source control valve of the leaking fluid;
- said switch when open activates said interface upon detecting the leaking fluid, said interface turning said control valve of the leaking fluid to a closed position for eliminating continuance of the leaking fluid.

13. The fluid leak detection system of claim 11, further including:
- a communications device electrically coupled to said switch;
- a monitoring station; and
- a communications link connecting said communications device to said monitoring station;
- said communications device automatically notifying said monitoring station of the leaking fluid when said switch activates said communication device.

14. The fluid leak detection system of claim 7, wherein said disinfecting liquid is an antimicrobial liquid to prevent mold and mildew growth.

15. A method for substantially preventing mold and mildew growth by said system according to claim 1, said method comprising the steps of:

a) providing said reservoir;

b) depositing a predetermined quantity of a disinfecting liquid into said reservoir;

c) connecting one end of at least one conduit to said reservoir;

d) closing a distal end of said at least one conduit to an initial closed position by folding said distal end onto an adjacent portion of said at least one conduit;

e) automatically opening said distal end of said at least one conduit to an open position upon detecting a leaking fluid disposed on a surface external of said at least one conduit such that said disinfecting liquid automatically discharges from said distal end and encounters the detected fluid to substantially prevent mold and mildew growth;

f) activating an alarm upon detection of depletion of general disinfecting liquid in said reservoir.

16. The method of claim 15, wherein step e) includes the steps of:

wrapping a leaking fluid-dissolvable member about said distal end and said adjacent portion of said at least one conduit such that said disinfecting liquid is prohibited from egress outwardly of said distal end;

disposing a leaking fluid absorbent member along said distal end of said at least one conduit by extending outwardly said leaking fluid absorbent member along a partial longitudinal length of said at least one conduit;

dissolving said fluid-dissolvable member when said fluid-dissolvable member becomes saturated and thereby permitting said at least one conduit to be unfolded; and allowing said disinfecting liquid to flow outwardly from said distal end of said at least one conduit.

17. The method of claim 15, further including the steps of:

disposing a support frame on a support surface adjacent an area likely to have a leaking fluid;

anchoring said reservoir to said support frame; and maintaining said reservoir at an elevated position above said distal end of said conduit so that said disinfecting liquid is allowed to freely flow downstream along said at least one conduit after said distal end is in said open position.

18. The method of claim 17, further including the steps of: locating an electrical switch between said reservoir and said support surface; connecting a low voltage electrical source to said alarm; and opening said switch upon general depletion of said disinfecting liquid in said reservoir and activating said alarm.

19. The method of claim 18, further including the steps of:

electrically coupling an interface to an existing fluid source control valve of the leaking fluid;

when said switch is open, activating said interface upon detecting the leaking fluid; and said interface turning said control valve of the leaking fluid to a closed position for eliminating continuance of the leaking fluid.

20. The method of claim 19, further including the steps of:

electrically connecting a communications device to said switch;

establishing a communications link between a monitoring station and said communications link; and said communications device automatically notifying said monitoring station of the leaking fluid when said switch activates said communication device.

* * * * *